United States Patent [19]
McGeehin et al.

[11] Patent Number: 6,046,054
[45] Date of Patent: Apr. 4, 2000

[54] SEMICONDUCTING OXIDE GAS SENSORS

[75] Inventors: Peter McGeehin, Compton; Patrick Timothy Moseley, Chilton; David Edward Williams, Abingdon; Geoffrey Stephen Henshaw; Darryl Hirst Dawson, both of London; Laura Jane Gellman, Harrow, all of United Kingdom

[73] Assignee: Capteur Sensors & Analysers, Ltd., Didcot, United Kingdom

[21] Appl. No.: 08/987,539

[22] Filed: Dec. 9, 1997

Related U.S. Application Data

[63] Continuation-in-part of application No. 08/387,794, Feb. 17, 1995, abandoned.

[30] Foreign Application Priority Data

Feb. 19, 1994 [GB] United Kingdom .................... 9403211

[51] Int. Cl.$^7$ ................................................ G01N 33/00
[52] U.S. Cl. ......................... 436/121; 436/122; 436/127; 436/128; 436/131; 436/132; 436/133; 436/134; 436/137; 436/139; 436/140; 436/141; 436/142; 436/151; 73/31.06; 422/90; 422/98; 422/95
[58] Field of Search .................................. 422/90, 95, 98; 436/106, 113, 116–122, 124, 127, 128, 131, 132–134, 136–137, 139–142, 149, 151; 73/31.05, 31.06; 204/153.13, 153.1, 153.14, 153.16; 338/24; 340/605, 634

[56] References Cited

U.S. PATENT DOCUMENTS 4,454,494 6/1984 Williams et al. ......................... 338/34
4,458,233 7/1984 Komine et al. ......................... 338/34

FOREIGN PATENT DOCUMENTS

| 2149122 | 6/1985 | United Kingdom . |
| 2166247 | 4/1986 | United Kingdom . |
| 2198844 | 6/1988 | United Kingdom . |
| 2202948 | 10/1988 | United Kingdom . |
| 9308467 | 4/1993 | WIPO . |

OTHER PUBLICATIONS

T. Ishihara et al, *Chem. Lett.* 1988, 997–1000.

M. Metikos–Hukovic et al, *Mat. Res. Bull.* 1988, 23, 1535–1544.

M. I. du Silva Pereira et al, *J. Chem. Soc., Faraday Trans. I* 1989, 85, 2473–2480.

S. Cheng et al. *J. Catal.* 1990, 122, 1–9.

M. Eibschutz et al. *Appl. Phys. Lett.* 1992, 60, 830–832.

T. Oyama et al. *J. Mater. Sci. Lett.* 1992, 11, 1573–1575.

*Primary Examiner*—Arlen Soderquist
*Attorney, Agent, or Firm*—Woodcock Washburn Kurtz Mackiewicz & Norris LLP

[57] ABSTRACT

The selectivity of response of resistive gas sensors to specific gases or vapors is improved by the selection of specified gas-sensitive materials which are not previously known for the applications described, which include detection of hydrocarbons in the presence of CO, $H_2S$, $SO_2$, chlorine, $NO_2$, $CO_2$ (especially in low concentrations), CFC's, ammonia, free oxygen by determination of partial pressures, and numerous organic gases and vapors.

11 Claims, 8 Drawing Sheets

SEMICONDUCTING OXIDE GAS SENSORS

CROSS-REFERENCE TO RELATED APPLICATIONS

This application is a continuation-in-part of the application of the same inventors, titled "Semiconducting Oxide Gas Sensors and Materials Therefor", filed Feb. 17, 1995, under application Ser. No. 08/387,794, abandoned.

BACKGROUND OF THE INVENTION

1. Field of the Invention

This invention relates generally to resistive gas sensors, and is more particularly concerned with a method for the use of sensor arrays comprising such sensors.

2. Discussion of the Prior Art

A resistive gas sensor, as is well known, comprises, in general terms, a semiconducting sensing element such that its electrical resistance changes in response to a change in the concentration of at least one gas or vapor (sometimes referred to as a "target gas") that is present, to a substantially greater extent than to other gases or vapors.

The sensor is thus selective in favor of the target gas and is accordingly used for detection, and, where required, measurement, of the target gas. Such a sensor will be referred to as a sensor of the kind specified.

Semiconducting oxide materials, when used for gas sensors, provide devices which are inexpensive, light and robust. However, they suffer a reputation for unacceptable cross-sensitivity to different gases, particularly to water vapor, which is always present in the atmosphere at concentrations which can vary widely. Devices based on tin dioxide, such as are widely use, show strong effects of changes in relative humidity, both on the baseline resistance and on the sensitivity of the resistance change to the presence of gases such as carbon monoxide.

These devices also have a reputation for excessive baseline drift and show a long stabilization time in the atmosphere after the temperature of the device has first been raised to its operating value.

SUMMARY OF THE INVENTION

The present invention aims to provide sensor materials that are more selective than those in current use, particularly in respect of the discrimination of changes in the concentration of the gas to be detected from the effects of varying relative humidity.

A second object of the invention is to provide sensor materials with short stabilization time and greatly reduced baseline drift in comparison with those devices that are currently in common use.

A third object of the present invention is to provide sensor materials which offer improved selectivity and sensitivity for certain gases whose detection in the environment is of concern, for example in breathing atmospheres or in the exhaust gases of combustion, and sensor materials useful for the measurement of reactive gases such as hydrogen sulfide in anaerobic atmospheres.

A fourth object is to provide certain combinations of sensors utilizing different materials which can then be used, in various ways well known in the art, to provide more reliable alarm indication for certain conditions that might be injurious to health and safety.

The present invention is based on the use of $Cr_{(2-x)}Ti_xO_3$, in which $0.3 \geq x \geq 0.5$, preferably $0.3 \geq x \geq 0.1$. This range of materials is useful for the measurement of volatile alcohol, aldehydes, including dialdehydes such as glutaraldehyde, ketones, such as butan-2-one, hydrocarbons other than methane, including gasoline, ethers, including diethers such as dimethoxyethane, and sulphur dioxide. It is useful for the measurement of hydrogen sulfide in anaerobic atmospheres, as in the measurement of concentrations of hydrogen sulphide in carbon dioxide. It shows particularly good baseline stability and discrimination against the effects of varying relative humidity.

BRIEF DESCRIPTION OF THE DRAWINGS

Preferred features of the invention will now be described, by way of example, with reference to the accompanying drawings in which.

DETAILED DESCRIPTION OF THE EMBODIMENTS

Figure 1:
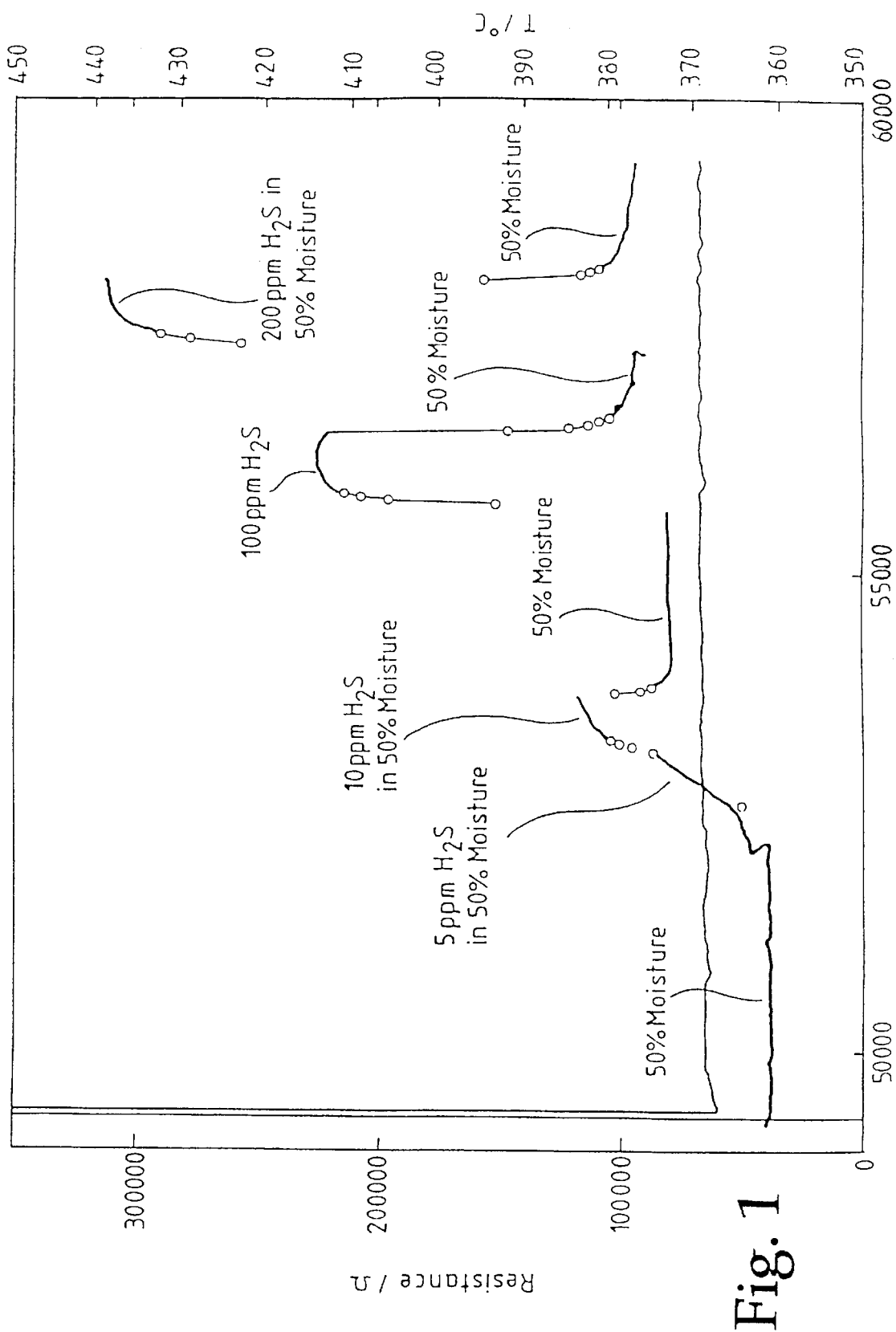
FIG. 1 is a diagram showing variation with time of the resistance of a sensor device composed of $Cr_{1.8}Ti_{0.2}O_{(3+x)}$ before being pretreated, when exposed to various small concentrations of $H_2S$ in air.

It has been suggested (in the paper by D. E. Wllliams and P. T. Mosely, J Materials Chemistry, 1 (1991) 809–814) that the behavior of semiconducting oxide materials can be manipulated by manipulation of the crystallite size and surface area per unit mass of the materials exposed to the gas, and of the concentration of electrically active donor species present in the lattice, so as to give changes characteristic either of n-type materials (resistance decreases in reducing gases and increases in oxidizing gases); or of p-type materials (resistance increases in reducing gases and decreases in oxidizing gases); or of mixed behavior.

The same paper also suggested that, by a fortuitous combination of the concentration of electrically active donors and the surface area per unit mass, some, selectivity to certain gases might be obtained.

In the light of these disclosures, it is possible to try substituting elements of different valency into some parent composition, and to try making variations in the preparation of materials so as to obtain different surface areas per unit mass, in an attempt to achieve a degree of selectivity.

However, the above paper offers no prescription for the choice of suitable parent compositions, and implies that wide selectivity might require specific interaction of the target gas with the surface, as well as turning of the composition and surface area. The paper therefore leads to a conclusion that the observation of a wide selectivity of response in a semiconducting oxide material would be rather surprising; and that, furthermore, it would be very surprising indeed to find a high degree of selectivity of response where no specific interaction with the surface were anticipated— for example, a high selectivity of response for hydrocarbons over carbon monoxide.

The above mentioned paper is silent on the question of discrimination of the effects of the desired target gas from the effects of variation in relative humidity. It will also be appreciated, especially from the study of the art of catalysis, that substitutions of different elements into a lattice can serve to vary the surface density and nature of the gas adsorption sites present on the surface of the material. Such sites are often classified as acidic or basic, according to whether they can interact with gases such as ammonia on the one hand or hydrogen sulfide or carbon dioxide on the other. For example, it is often said that the substitution of chromium into a lattice serves to increase the acidity of the surface sites. However, it is by no means clear how such adsorption sites couple into the charge carriers present in the solid, so that a change in the adsorption of dissociation of a gas molecule on such a site could give rise to a change in the measured conductivity of the solid material.

Chromium titanium oxide sensors for Hydrogen Sulphide, for use in both aerobic and anaerobic environments The document GB-A-2 202 948 discloses compositions of general formula $Cr_2Ti_{(2-x)}O_{(7-2x)}$, where $2>x>0$, claiming these as selective ammonia sensors. The document states that sensors in accordance with that invention may be such that they do not suffer significant interference from other reducing gases commonly encountered (e.g., $H_2$, CO, $CH_4$, $C_2H_4$). The examples given are $TiO_2$—48.7 mol %, $Cr_2O_3$ ($Ti_{0.51}Cr_{0.97}O_{(2-x)}$) and $TiO_2$—90 mol % $Cr_2O_3(Cr_{1.8}Ti_{0.1}O_{(3+)})$. "Techniques and Mechanisms in Gas Sensing", ed. P. T. Moseley, J. O. W. Norris and D. E. Williams, p. 136, and Moseley and Williams, Sensors and Actuators B 1 (1990) 113.5, disclose $Ti_{0.9}Cr_{0.1}O_{(2-x)}$ as an unselective material, and $Cr_{1.8}Ti_{0.2}O_3$ as a material selective to ammonia.

Surprisingly, we have now found that chromium titanium oxides can be formed into sensor elements which are extremely sensitive to hydrogen sulphide.

We have also found, again to our surprise, that the response of $Cr_{1.8}Ti_{0.2}O_{3+x}$ to $H_2S$ is greatly enhanced, in both amplitude and speed of response, by prior treatment of the sensor in an atmosphere containing $H_2S$: an example of such a pretreatment is exposure for a time of a few minutes (between 1 and 10 minutes) to a concentration of 10 ppm of the gas, at a sensor temperature of greater than about 200° C. and less than about 600° C. Longer times of exposure, and higher gas concentrations, may be used, but do not give any further enhancement of performance. Sensors prepared in this way have the particular advantage that the interference caused by changes in relative humidity is very small in comparison with the response to hydrogen sulphide: the effect of a change in relative humidity from 0 to 100% at room temperature is equivalent to the response to 10.3 ppm of $H_2S$ when the sensor is operated at 400° C. When the pretreated sensor is operated at 250° C., relative sensitivity to $H_2S$ is even higher.

This pretreatment (or preconditioning) leads to a modification of the surface of the material, which can be detected either by photoelectron spectroscopy, or other such surface analytical method, or, conveniently, by temperature programmed desorption. In the latter method, the device is heated in a vacuum and the gases desorbed are detected, for example using a mass spectrometer.

The effect of the pretreatment appears to be permanent at the operating temperature for $H_2S$ detection, and is characterized by an increase of the baseline from that of the virgin material, and a dramatic increase in the sensitivity and speed of response. Temperature-programmed vacuum-desorption studies of the treated materials showed a loss of $SO_2$ from the surface at temperatures above 630° C.

The $H_2S$ pretreatment of $Cr_{1.8}Ti_{0.2}O_3$ has been studied by x-ray photo-electron spectroscopy (XPS). As the pretreatment progressed, the S 2p region of the spectra changed. Initally, three peaks were observed: two major peaks at binding energies of 159.0 eV and 164.4 eV, tentatively assigned to sulphide and elemental sulphur species, respectively, and a minor peak at 168.5 eV, attributed to sulphate groups formed on the surface. When the pretreatment was complete, as judged by the effects on the gas response, only a single peak at 168.7 eV was present.

The sensor material was prepared by reacting mixed powders of $Cr_2O_3$ and $TiO_2$ at 800° C. A sensor was prepared by depositing by standard thick-film ceramic fabrication methods, a porous layer of the sensor material over an inter-digitated pattern of gold electrodes supported on an alumina substrate. On the reverse side of the substrate was printed a platinum track. The device was heated by applying a current to the platinum track using a Wheatstone bridge arrangement to keep the platinum track at constant resistance and hence constant temperature.

FIG. 1 shows the resistance-time variation of a sensor device of composition $Cr_{1.8}Ti_{0.2}O_3$, on initial exposure to small concentrations of $H_2S$ in air, at an operating temperature of 370° C. The baseline shift caused by the first exposure is clear.

Figure 2:
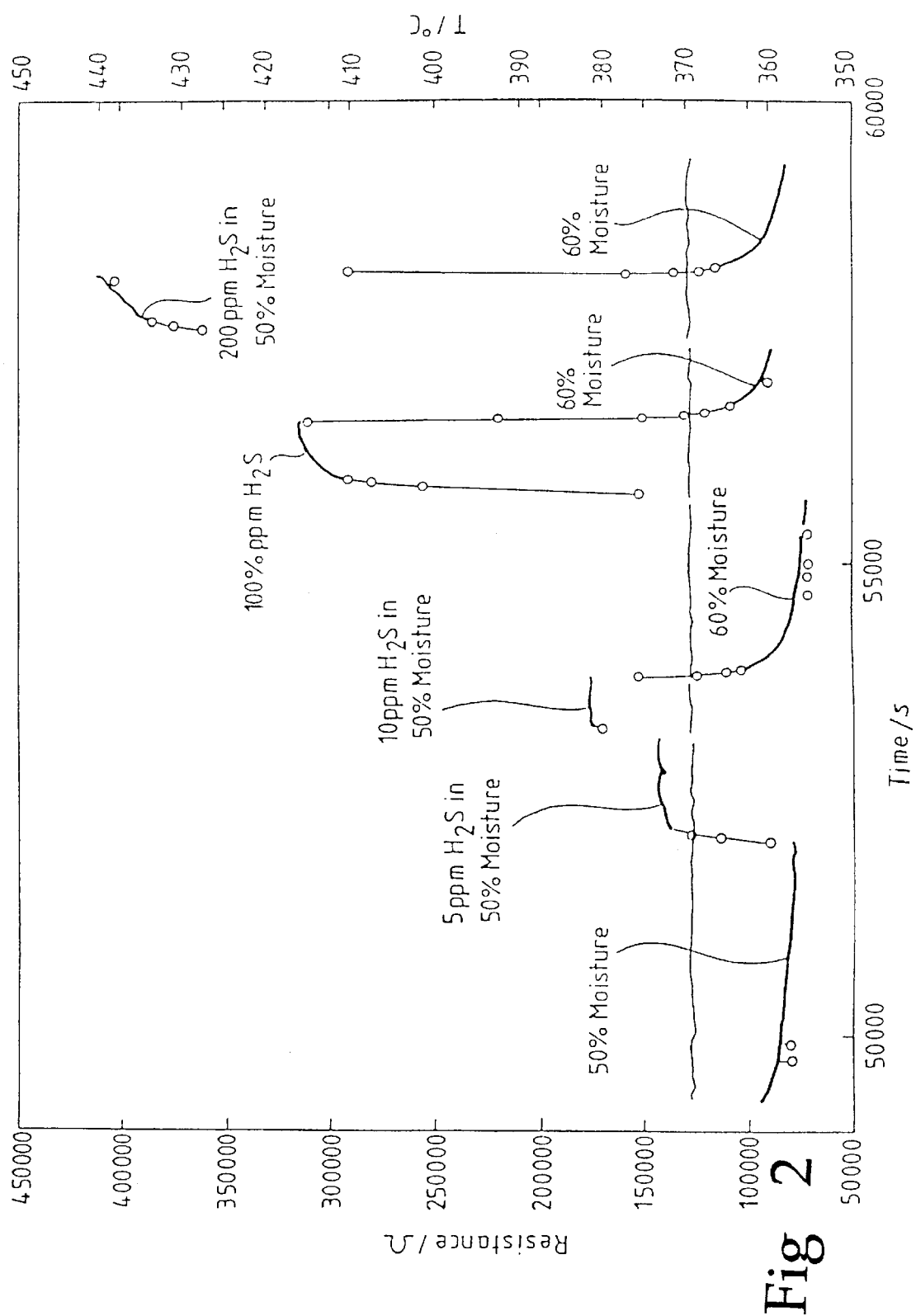
FIG. 2 is similar to FIG. 1 for the same device after pretreatment.

FIG. 2 shows subsequent gas exposures. In contrast to the first exposure, the response to 5 ppm gas is now rapid and substantial. In both FIGS. 1 and 2, the left hand scale and the line without symbols show the temperature (370° C.). "50% moist" means a relative humidity of 50% in clean air.

Figure 3A:
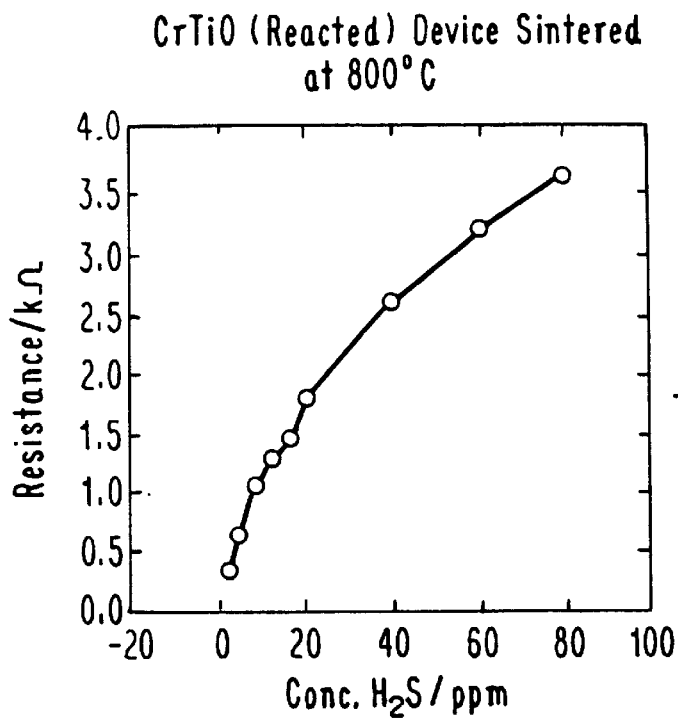
FIGS. 3a and 3b consists of a resistance-gas concentration diagram for a similar pretreated device in $H_2S$, and, below it, a similar diagram for the ratio $(R_{gas}-R_{air})/R_{air}$.
Figure 3B:
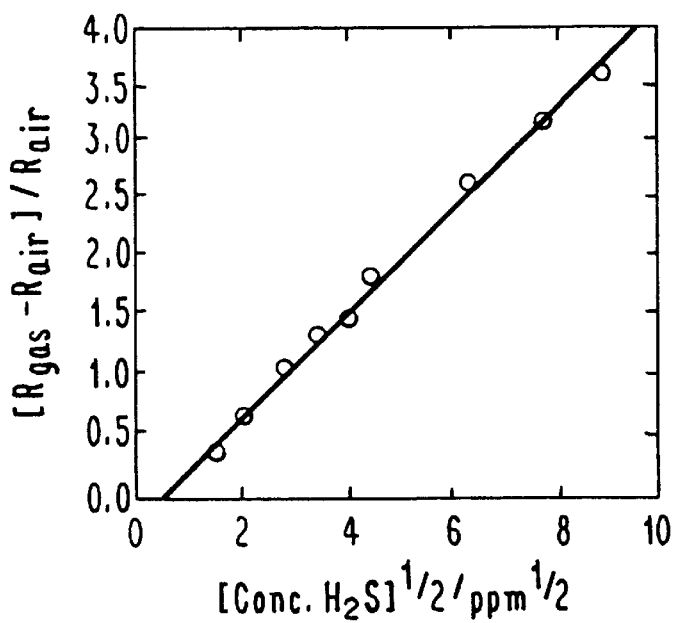

FIG. 3 shows the gas response law for a pretreated similar sensor, at 370° C., illustrating the dependence on the square root of the concentration. In the lower diagram of FIG. 3, the ratio of $(R_{gas}-R_{air})$ to $R_{air}$ shows a straight line relationship when plotted against the square root of gas concentration, where $R_{gas}$ and $R_{air}$ are the resistance in the gas and in air, respectively.

The response, at temperatures appropriate to the detection of hydrogen sulphide ($\leq 400°$ C.), of the pretreated sensor to methane, hydrogen, hydrocarbons and carbon monoxide, present in the air, was very small so that these sensors are very useful for the detection of hydrogen sulphide in a background of such gases. Circumstances where such selectivity is of importance include monitoring for hydrogen sulphide around a natural gas installation.

Figure 5:
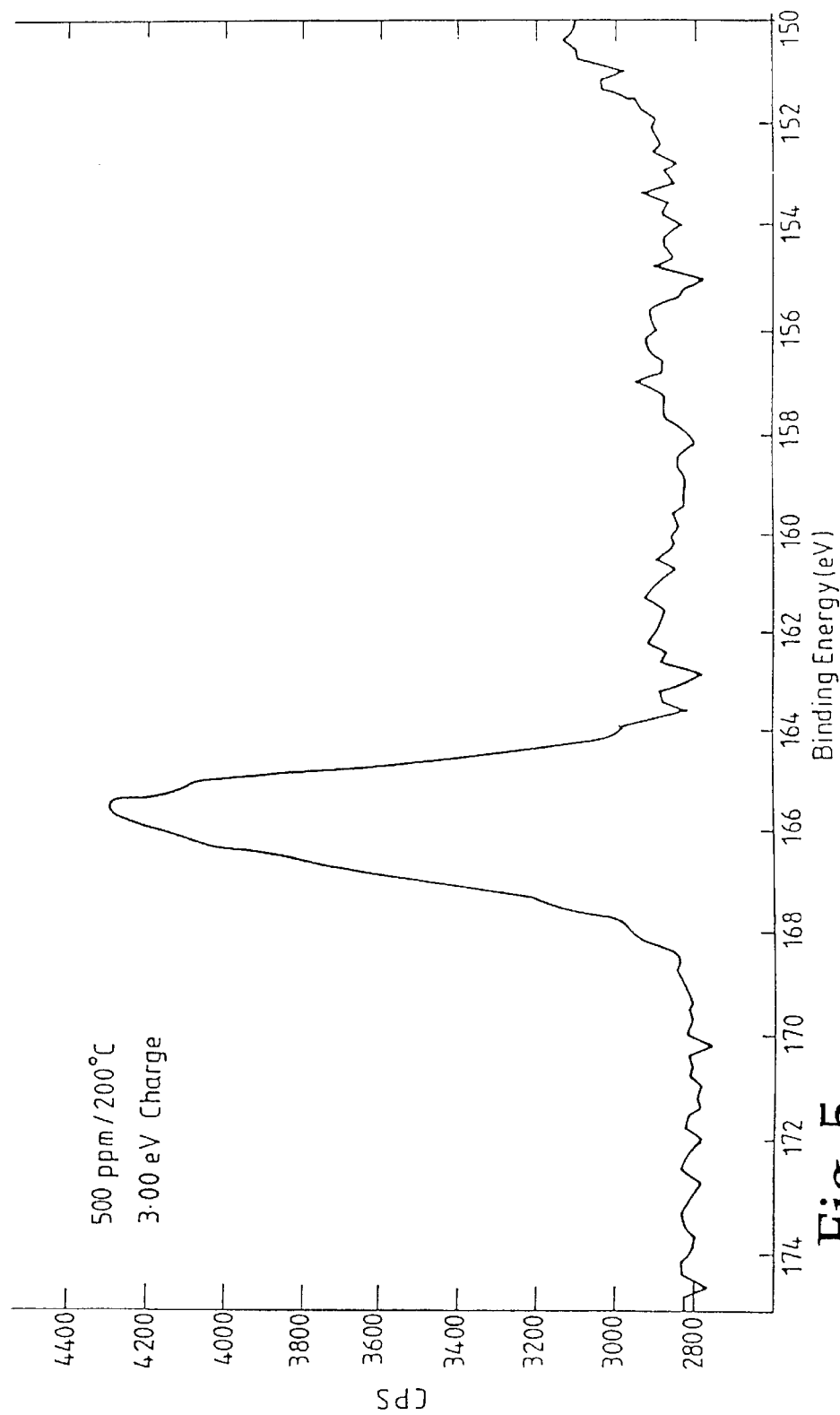
FIG. 5 is similar to FIG. 4 for the same specimen when fully pretreated.
Figure 8:
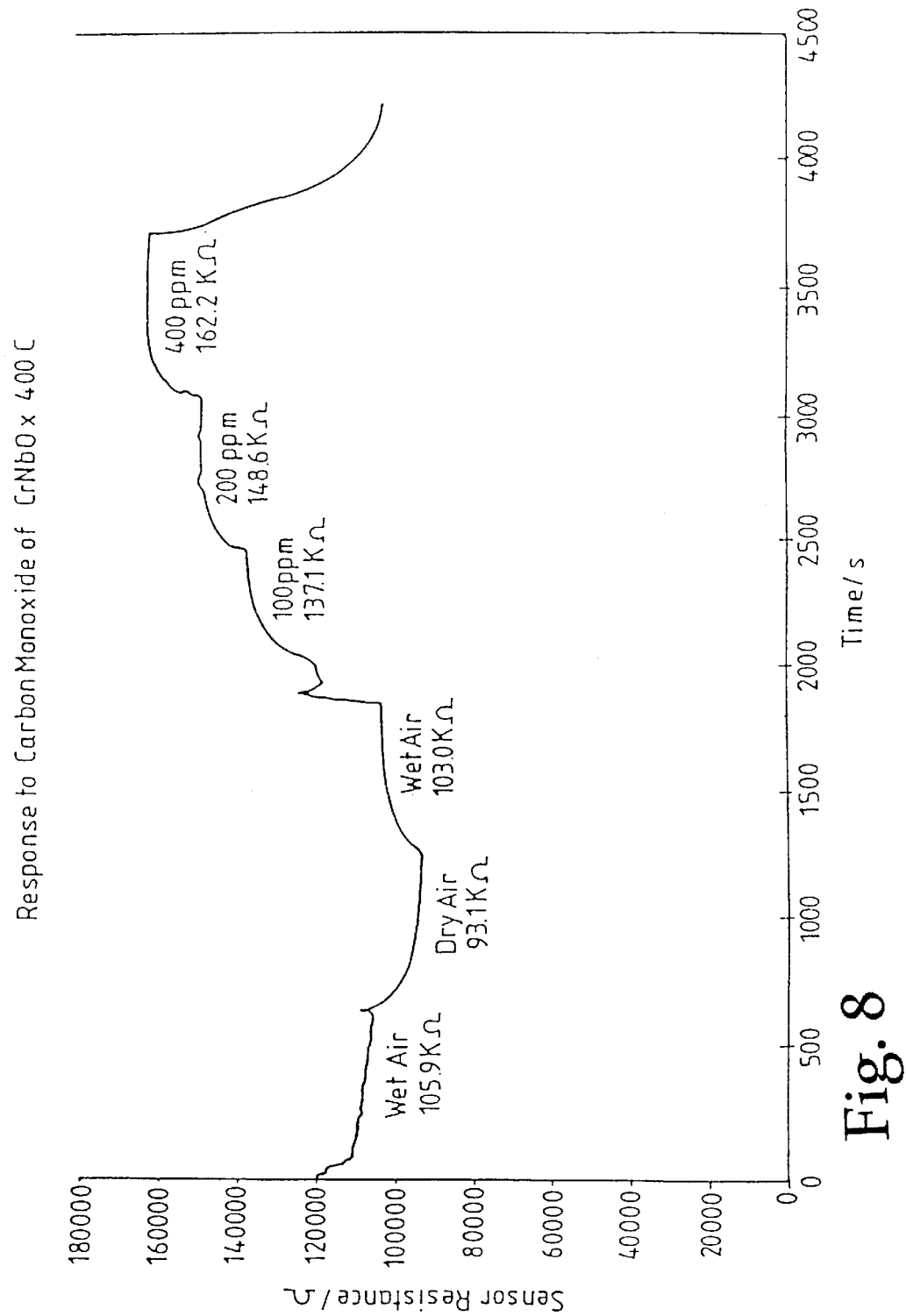
FIG. 8 is a resistance/time diagram for a chromium-niobium oxide sensor, showing its response to various concentrations of CO in air.

Pretreatment can be detected by x-ray photoelectron spectroscopy (XPS) of the sensor surface. FIG. 8 shows an XPS spectrum of a partially treated specimen (exposure to 1 ppm $H_2S$ at 200° C.). It should be noted that, because of an instrument effect, the binding energy scale on this diagram has to be increased by 3.6 eV. FIG. 5 shows an XPS spectrum of a completely treated specimen (50 ppm exposure at 200° C.). The binding energy scale on this diagram is too low by 3 eV.

The literature on the behavior of semiconducting oxides as sensors for reactive gases universally and unambiguously states that such detection requires the presence of oxygen, preferably at levels such as are found in the air. We have now found that chromium titanium oxides can be used to measure low concentrations of hydrogen sulphide in an anaerobic or substantially anaerobic environment, such as pure carbon dioxide. In this case, also, pretreatment with hydrogen sulphide enhanced the response. Such sensors are useful in the control of processes such as anaerobic fermentation.

The response of a sensor, pretreated as above, to hydrogen sulphide in carbon dioxide is as follows:

Composition: $Cr_{1.8}Ti_{0.2}O_3$

Operating temperature: 400° C.

Resistance in pure $CO_2$: 80 kohm

Resistance in pure $CO_2$ containing 500 ppm $H_2S$: 770 kohm

Chromium titanium oxide sensors for hydrocarbons and carbon monoxide, with improved baseline stability and rejection of effects of varying relative humidity Tin dioxide and compositions derived from and largely comprising tin dioxide are widely cited in the art and are used in gas sensitive resistors. However, devices fabricated from tin dioxide show a very large baseline drift on being heated to the operating temperature: a change of more than 100% over a period of 12 hours is not uncommon. Furthermore, this drift can continue for a period of weeks or even months, necessitating constant checking and recalibration. The baseline resistance of tin dioxide devices is also very sensitive to changes in relative humidity: typically, the resistance will halve if the atmosphere is changed from one which is dry (<2%RH) to one which wet (>70%RH). The sensitivity to carbon monoxide is also greatly affected by changes in the ambient relative humidity.

Although the previous literature implies that compositions of chromium titanium oxide which are chromium-rich should be insensitive to hydrocarbons and carbon monoxide, we have now been surprised to find that sensors prepared from these materials, as described herein, can be operated at a temperature such that the response, at concentrations of importance for health and safety monitoring, to propane (operating temperature 475° C.), and to carbon monoxide (operating temperature 320° C.–390°) is substantially greater than the interference caused by a change of relative humidity between 0 and 100% at room temperature.

In contrast to the behavior exhibited by tin dioxide, sensors fabricated from these materials reach a stable resistance within five minutes of being energized, and show a subsequent baseline drift of less than 0.5% per month. These materials therefore form sensors of great utility for carbon monoxide and hydrocarbons other than methane. The responses to methane and hydrogen are very small, so the sensors are very useful for the detection of carbon monoxide in the presence of a background of methane an/or hydrogen. Circumstances where such a selectivity is of importance include monitoring for carbon monoxide in a coal mine, or in the monitoring for leakage of carbon monoxide from domestic gas-fired appliances.

Figure 6:
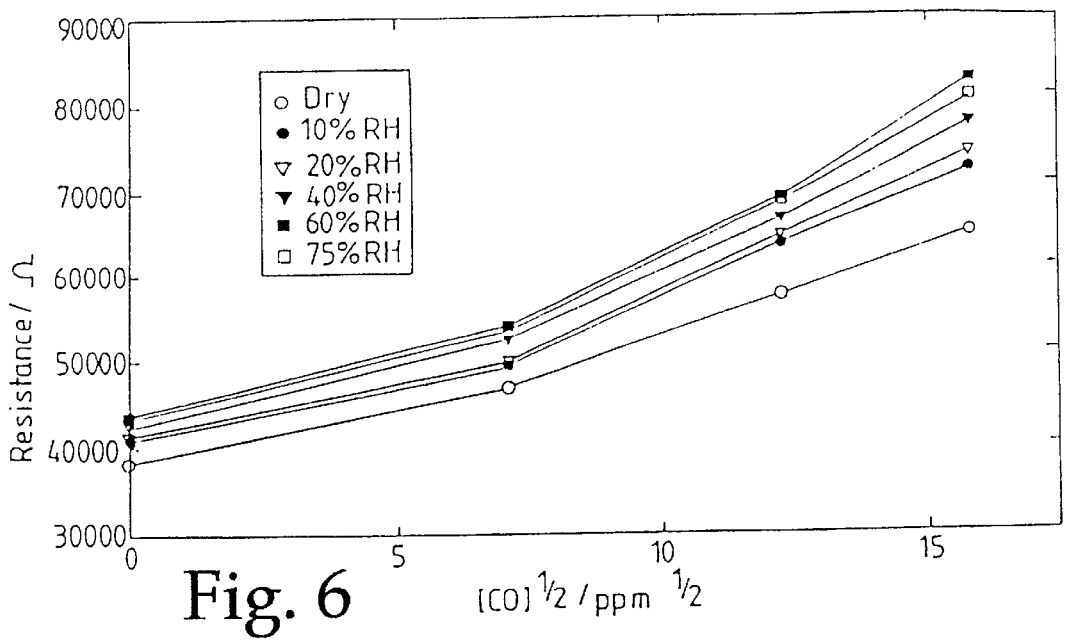
FIGS. 6 and 7 show the response to CO of chromium-titanium oxide sensor, in terms of resistance plotted against a function of CO concentration for various values of humidity, at two different temperatures.
Figure 7:
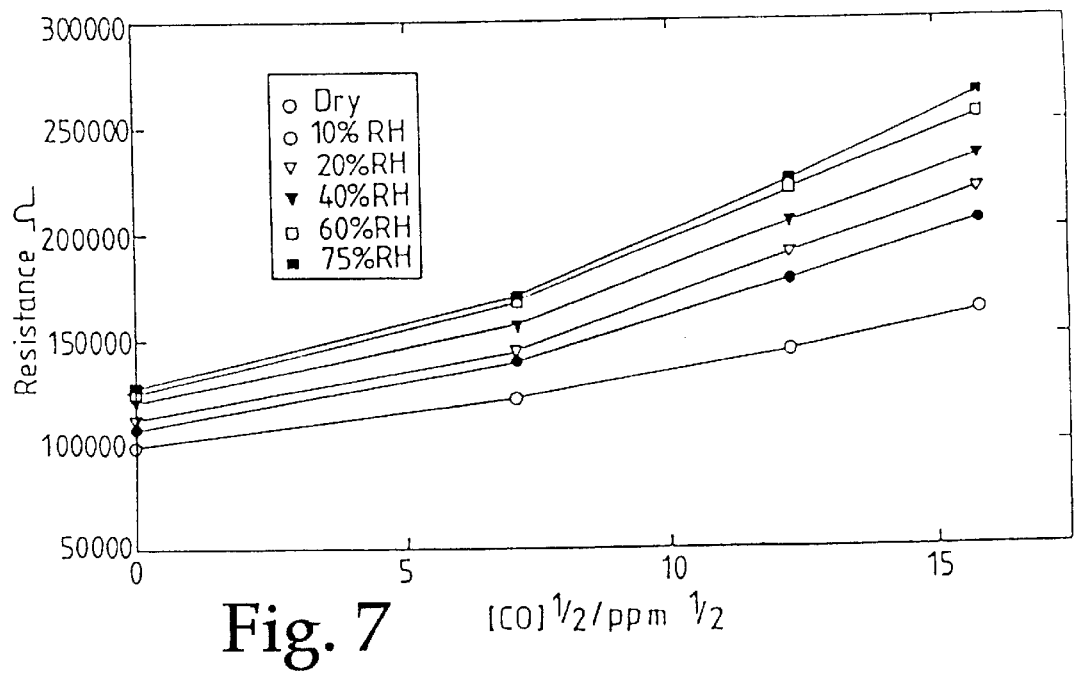

FIGS. 6 and 7 show the response of a $Cr_{1.8}Ti_{0.2}O_3$ sensor to various concentrations of carbon monoxide in the air, at various temperatures and relative humidities (referred to an ambient atmosphere at 20° C.), and at 415° C. in FIG. 6 and at 370° C. in FIG. 7. The response is larger at lower temperature, but if the temperature is too low, then an effect of variation of relative humidity on the sensitivity to CO becomes apparent. The chosen operating temperature of 390° C. represents a satisfactory compromise in which the response is adequately large and the effect of relative humidity changes rather small.

In general, the material shows a resistance increase in response to the presence of reducing gases in the atmosphere, and the ratio of resistance in the presence of the gas to resistance in the absence of the gas increases with the square root of the gas concentration.

Exposure to hydrogen sulphide at temperatures between 150° C. and 400° C. has the effect of considerabby diminishing the response to carbon monoxide, and to other gases for which the operating temperature is below approximately 450° C.

Table 1 shows that a range of compositions in the series $Cr_{(2-x)}Ti_xO_3$ is sensitive to carbon monoxide, and has the characteristic that the effect of a change in relative humidity from zero to 100% gives a signal equivalent to only a small concentration of carbon monoxide (the number is given as the "figure of merit" in Table 1).

TABLE 1

Response to 300 ppm carbon monoxide in the air (50% relative humidity at 20° C.) of sensors fabricated from a range of compositions in the series $Cr_{(2-x)}Ti_xO_3$

| x | (Resistance in presence of CO)/(Resistance in the absence of CO | Figure of merit (ppm CO equivalent of change in relative humidity from zero to 100%) |
|---|---|---|
| 0.05 | 2.6 | 0.67 |
| 0.10 | 4.3 | 0.66 |
| 0.15 | 4.3 | 0.5 |

Chromium titanium oxide sensors for sulphur dioxide

Although many sensor materials show resistance response to the presence of sulphur dioxide, the problem with measurement of this gas using this technology is that the sensors often rapidly become poisoned. Sometimes this is due to the formation of metal sulphates which are molten at the operating temperature. Sometimes it is because of an irreversible adsorption of the gas.

It is not obvious how to choose a material that gives a satisfactory response to $SO_2$, which is small in comparison with the effects of change in relative humidity, and which also is not poisoned by the presence of the gas and shows a reversible response. Table 2 shows that a sensor made from $Cr_{1.8}Ti_{0.2}O_3$ shows a satisfactory response in comparison with the effects of changes in relative humidity. We have further found that such sensors are stable in the presence of the gas, even at high concentration (e.g. 2000 ppm), and do not age or become poisoned. Other sensors of the general formula $Cr_{(2-x)}Ti_xO_3$, where $0.3 \geq x \geq 0.1$, are by and large equally effective.

Table 2

Sensors response to sulphur dioxide compared with response to change in relative humidity Composition: $Cr_{1.8}Ti_{0.2}O_3$ Operating temperature: 500° C.

Resistance in dry air: 10 kohm

Resistance in wet air:

(100%RH at 20° C.): 12 kohm

Resistance in dry air containing 400 ppm $SO_2$: 15 kohm

Sensors, and combinations of sensors, for various volatile organic compounds (a) Chromium titanium oxide sensors Table 3, below, shows the response of sensors fabricated from $Cr_{1.8}Ti_{0.2}O_3$ to a range of organic vapors, compared with the effect of a change in relative humidity from 0 to 100%. The effects of the organic vapors are large in comparison with the effects of water vapor, and in some cases are very large. The previous disclosures that are concerned with compositions including those in the range $Cr_{(2-x)}Ti_xO_3$ implied that these compositions were insensitive to such vapors. The result exemplified in Table 3 is therefore surprising. We ascribe this result to differences in the detail of the preparation: in particular, we have found that a microstructure comprising very small crystallites (<1 μm average diameter) with a very fine scale porosity (average pore diameter <1 μm) is necessary to confer such strong sensitivity.

TABLE 3

Response of sensors fabricated from $Cr_{1.8}Ti_{0.2}O_3$ to a range of organic vapors, compared with the effect of a change in relative humidity from 0 to 100%

| Gas | Concentrations/ppm | Operating temperature/ °C. | Resistance ratio: $R_{gas}/R_{air}$ |
|---|---|---|---|
| water vapor | 100% RH at 20° C. | 400 | 1.2 (compared with dry air |
| propane | 1000 | 475 | 1.4 |
| butane | 1000 | 475 | 1.4 |
| hexane | 3000 | 475 | 2.7 |
| hexane | 3000 | 400 | 3.1 |
| petroleum (gasoline) | vapor above liquid at 20° C. | 475 | 5.6 |
| methanol | 1000 | 460 | 3.1 |
| methanol | 1000 | 250 | >3.5 |
| ethanol | 1000 | 460 | 2.8 |
| ethanol | 1000 | 250 | >3.1 |
| propan-2-ol | 200 | 400 | 8.4 |
| acetone | vapor above liquid at 20° C. | 500 | 9 |
| butan-2-one | vapor above liquid at 20° C. | 475 | 6.3 |
| glutaraldehyde | 1 | 400 | 1.2 |
| glutaraldehyde | 3 | 400 | 1.5 |
| dimethoxyethane | 5000 | 500 | 5,7 |

(b) Chromium iron niobate sensor used in sensor array with $Cr_{1.8}Ti_{0.2}O_3$ Table 4, below (and see also FIG. 8), shows the response of sensors fabricated from $CrNbO_4$ and $Fe_{(1-y)}Cr_yNbO_4$, where $0 \leq y \leq 1$, to a variety of organic vapors. The pattern of responses is different from that of $Cr_{(2-x)}Ti_xO_3$, and furthermore is also different from that shown by sensors made from $SnO_2$, or $SnO_2$ doped with precious metals (Pt, Pd etc.), such as are common in the art. Therefore, combinations of such sensors can usefullly be deployed in a sensor array, e.g. a so-called "electronic nose", to discriminate between different vapors, using pattern-recognition methods, or principal component analysis, or standard methods of multivariate regression. The use of sensor materials such as those described here will confer advantage because such materials have such different patterns of response. Furthermore, the materials are much less sensitive to the effects of variable relative humidity, and are much more stable than those previously described: these attributes are particularly important in a sensor array system.

FIG. 8 shows that a sensor made of $CrNbO_4$ is particularly suitable for detection of CO.

TABLE 4

Response of chromium iron niobates to various organic gases/vapors, compared with the effect of a change in relative humidity between zero and 100%

| Sensor material | gas | concentration /ppm | operating temperature/° C. | Resistance $R_{gas}/R_{air}$ |
|---|---|---|---|---|
| $CrNbO_4$ | water vapor | 100% RH at 20° C. | 500 | 1.15 (compared with dry air) |
| $CrNbO_4$ | acetone | vapor over liquid at 20° C. | 500 | 13.8 |
| $CrNbO_4$ | dimethoxyethane | 5000 | 500 | 4.0 |
| $CrNbO_4$ | hexane | 3000 | 500 | 2.3 |
| $CrNbO_4$ | petroleum | vapor over liquid at 20° C. | 500 | 9.0 |
| $Fe_{0.92}Cr_{0.08}NbO_4$ | methylmethacrylate | 20 | 500 | 0.73 |
| $Fe_{0.92}Cr_{0.08}NbO_4$ | methylmethacrylate | 80 | 500 | 0.58 |
| $CrNbO_4$ | CO | 400 | 400 | 1.94 (compared with dry air) |

Figure 12:
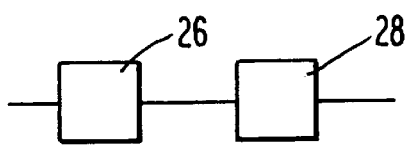
FIG. 12 shows a sensor array according to the invention.
Figure 4:
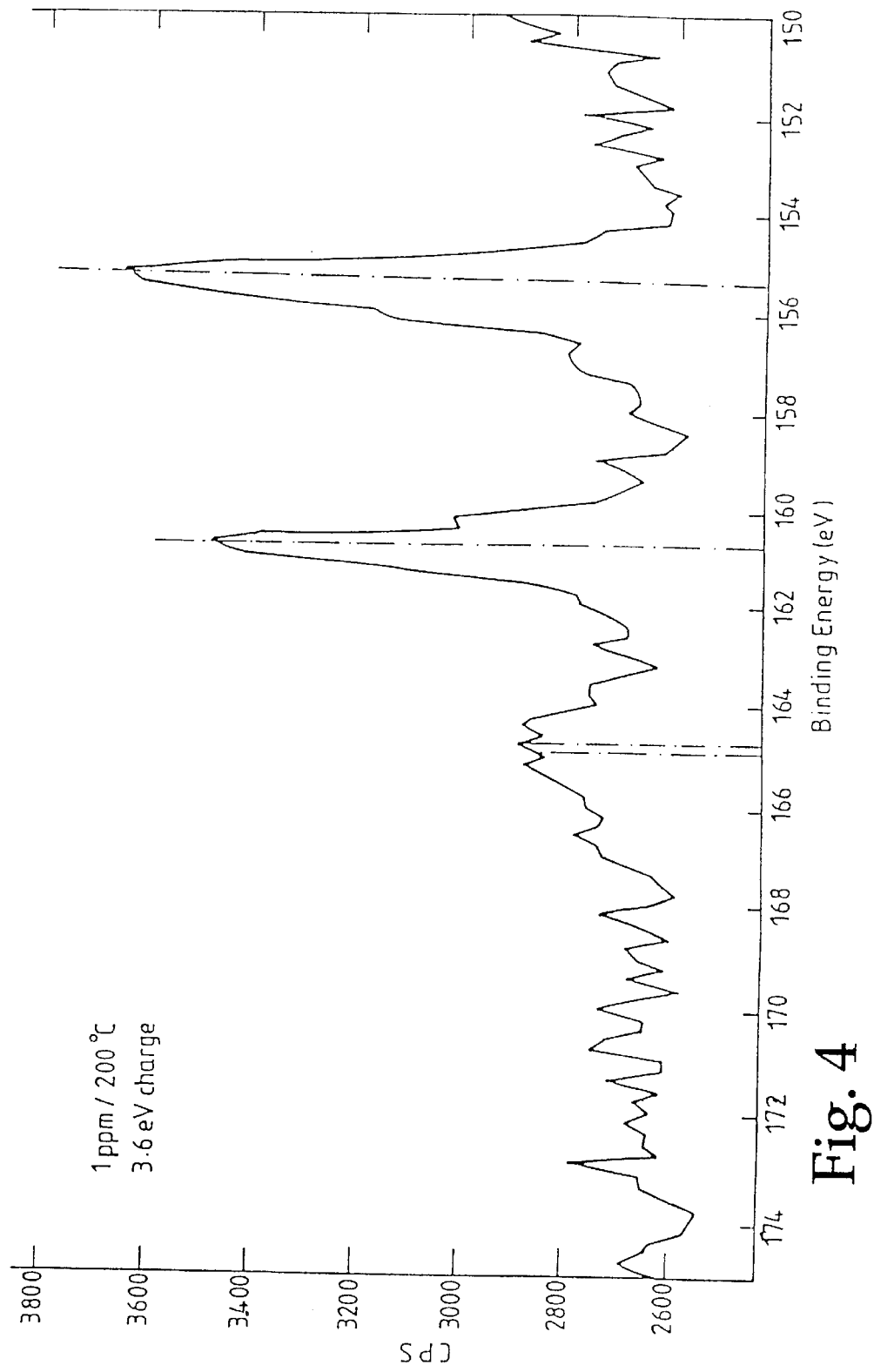
FIG. 4 shows an X-ray photoelectron spectrum for a chromium-titanium oxide specimen, partially pretreated.

Barium antimony stannate sensors used in a sensor array with $Cr_{(2-x)}Ti_xO_3$ (FIG. 12)

Surprisingly, we have now found that $BaSnO_3$ exhibits a useful sensitivity to the presence of small concentrations of carbon dioxide in the air. We have further found that, although the presence of CuO serves to increase the speed of response somewhat, the main effect of CuO is to lower the electrical resistance of the composite into a range where measurements are more easily made. Even more surprisingly, and in direct contradiction to the presumptions arising from the earlier work cited above, we have found that the electrical resistivity of $BaSnO_3$ can be satisfactorily lowered by replacing a fraction of the Sn in the formula by a pentavalent element, particularly Sb, and that sensors prepared from the resulting material show an electrical resistance varying by a useful amount in response to the presence of small additional concentrations of carbon dioxide in the air.

Figure 9:
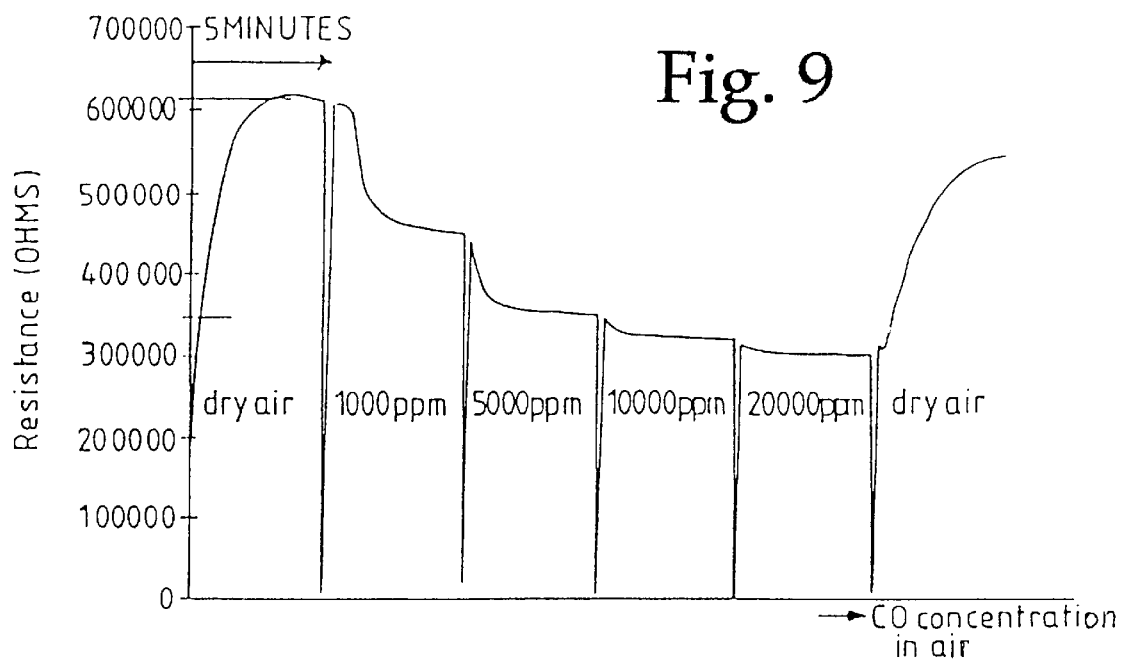
FIG. 9 is a response diagram showing variation in the resistance of a barium-tin-antimony oxide sensor with time, in response to various concentrations of CO in air; and, FIGS. 10 and 11 show, respectively, cross-sections through a gas sensor according to the invention.

In an example, a material of composition $BaSn_{0.99}Sb_{0.01}O_3$ was prepared by conventional ceramic fabrication techniques, mixing powders of $BaCO_3$, $SnO_2$ and $Sb_2O_5$ in the appropriate proportions and firing in a furnace at 800° C. A sensor was prepared on a self-heated, planar substrate, as above, using conventional screen-printing fabrication methods. FIG. 9 shows the variation in electrical resistance of this sensor element in response to changes in the concentration of carbon dioxide in the air, being plotted over successive 5-minute periods, all at 350° C.

$BaSnO_3$ also, as disclosed in the document GB-A-2 149 121, shows resistance changes in response to the presence of small concentrations of reactive and flammable gases in the atmosphere. In order to distinguish such changes from those caused by variations in the concentration of carbon dioxide, a sensor 26 comprising $BaSn_{(1-z)}Sb_zO_3$ (0<z<0.1) as the sensitive element can be combined with another sensor 28 which responds to the presence of reactive gases, but which does not respond to the presence of small concentrations of $CO_2$, ie. $Cr_{(2-x)}Ti_xO_3$ having the advantage of a relatively low response to the effect of changes in relative humidity, as discussed above. The interfering effect of changes in relative humidity on the sensor of composition $BaSn_{(1-z)}Sb_zO_3$ can be mitigated by using it in conjunction with a humidity sensor of conventional design, e.g. a capacitive device utilizing aluminum oxide as the sensitive element.

Combinations of sensors useful for the monitoring of leaks of ammonia and chlorofluorocarbon refrigerants Tin dioxide is useful as a sensing element material in a gas-sensitive resistor responding to the presence of small concentrations in the air of chlorofluorocarbons (CFC) such as $CF_2Cl_2$ (also known as R22). These agents are widely used as refrigerants but they have severe effects on the concentration of ozone in the upper atmosphere, so any leakage must be reliably and immediately detected. However, tin dioxide as a sensing element material suffers from the disadvantage of a strong effect of variations in relative humidity and also a strong response to many other reactive gases which might be present in the atmosphere, such as carbon monoxide emitted from internal combustion engines, or solvent vapors from cleaning agents, packaging and glue.

In particular, also, $SnO_2$ shows a strong response to ammonia, which is also widely used as a refrigerant, and which may be used in conjunction with chlorofluorocarbons such as R22. In such case, it is important to be able to distinguish a leakage of CFC from a leakage of ammonia. Sensors prepared with $Cr_{(2-x)}Ti_xO_3$ as the gas-sensitive resistor element have, as noted above, a response to organic vapors, including carbon monoxide, and, as previously disclosed in GB-A-2 202 948, ammonia. However, they are relatively insensitive to variations of relative humidity (as disclosed above); importantly, they are also insensitive to the presence of a CFC (R22).

Therefore, a pair of sensors, one of which utilizes $SnO_2$ and the other $Cr_{(2-x)}Ti_xO_3$, will be able to distinguish a leak of CFC (signal only on $SnO_2$) from one of ammonia (signal on both sensors), or a leak of CFC (signal only on $SnO_2$), from the presence of solvent vapors or carbon monoxide (signal on both sensors).

A combination of these two sensors with humidity sensor of conventional design, e.g. a capacitive device utilizing aluminum oxide as the sensitive element, will be able to discriminate all interferences. The humidity sensor, being unaffected by the refrigerant gases or by solvent vapors at environmentally significant concentrations, then provides a signal to compensate for the effect of relative humidity changes on the tin dioxide element, whilst the $Cr_{(2-x)}Ti_xO_3$ provides a signal to compensate for the presence of solvent vapors.

Discrimination between the effects of ammonia and the effects of solvent vapors, and consequent avoidance of false alarms, can also be obtained by using a combination of a sensor fabricated from $Cr_{(2-x)}Ti_xO_3$ with one fabricated from $Fe_{(1-y)}Cr_yNbO_4$ ($0 \leq y \leq 1$). For example, Table 5, below, shows a comparison of the response of these different materials to ammonia.

Comparison of the results in Table 5 with those in Tables 3 and 4 shows that $CrNbO_4$ is much less sensitive to ammonia than $Cr_{1.8}Ti_{0.2}O_3$, but that it is equally, or more, sensitive to solvent vapors. A simple comparison of the signal from two such sensors would then give a false alarm due to the presence of solvent vapor.

However, in a sensor array comprising such a combination of sensor, if the signal from the $Cr_{1.8}Ti_{0.2}O_3$ sensor is greater than that from the $CrNbO_4$ sensor, then ammonia is present; if it is less, then solvent vapors are present. Tables 4 and 5 show that similar combination of $Cr_{1.8}Ti_{0.2}O_3$ with $Fe_{(1-y)}Cr_yNbO_4$, ($0 \leq y \leq 1$) can be devised. Furthermore, a combination of these two sensors with a sensor fabricated from $SnO_2$ would, as described above, allow discrimination of solvent vapors, ammonia and CFC such as R22.

TABLE 5

Comparison of response to 100 ppm ammonia in air, of sensors fabricated from various materials

| Sensor material | Operating temperature/° C. | Resistance in 100 ppm $NH_3$ in dry air/Resistance in dry air |
|---|---|---|
| $Cr_{1.8}TiO_{.2}O_3$ | 430 | 1.77 |
| $CrNbO_4$ | 500 | 1.27 |
| $Fe_{0.92}Cr_{0.08}NbO_4$ | 500 | 0.53 |

Figure 10:
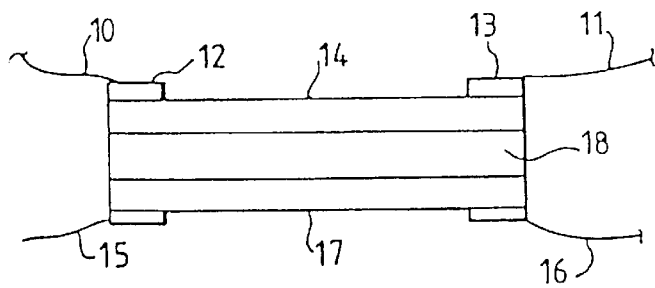

Sensor configurations with reference to the electrical interrogation of the gas sensitive materials FIG. 10 shows, purely diagrammatically, the conventional configuration of a semiconductor gas sensor, whereby the latter has four wires for electrical connection. Two of these, 10 and 11, are attached to a pair of electrodes 12 and 13, which are bridged by the gas sensing element 14, the resistance of which is to be measured. The other two wires 15 and 16 supply a resistance heating element 17, which is typically electrically insulated from the sensing element 14, for example by a layer of alumina 18 with the heating element 17 on one side and the sensing element 14 on the other.

When sensor element materials are used that have a resistance within a suitable range of values, however, it is possible to use fewer wires, with the advantage that heat loss by conduction is reduced. The sensor can then achieve its operating temperature with reduced power input.

Figure 11:
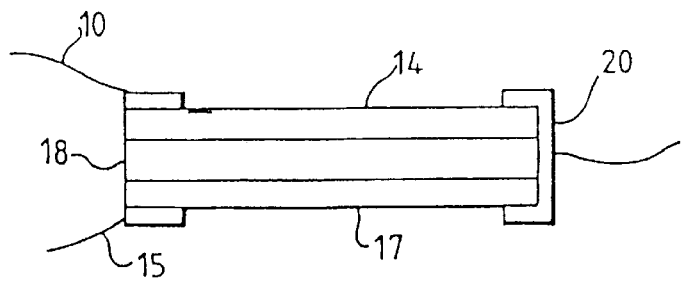

For example, when the resistance of the sensing materials during operation remains high with respect to the resistance of the heating element, then it is possible for the sensing part and heating part to have one wire 20 in common, thus reducing the number of wires to three as seen in FIG. 11.

Again, when the resistance of the sensing element material at the operating temperature is of similar magnitude to that of the heating element it is possible to have the sensing element in contact with the heater, as a parallel resistor, i.e. omitting the layer 18. Gas sensing will then be achieved by measuring the combined resistance, through two wires only.

These alternative interrogation configurations can be applied, with advantage, to any sensor made with the materials disclosed herein.

What is claimed as invention is:

1. In the method of detecting the presence of a target gas, wherein said method comprises the steps of exposing a sensor to an atmosphere that may contain said target gas, and measuring the electrical resistance of said sensor, the improvement wherein said sensor includes a sensor element formed of $Cr_{(2-x)}Ti_xO_3$, where $0.3 \leq x \leq 0.05$, and said target gas is a hydrocarbon other than methane, alcohols, aldehydes, ketones, ethers, esters, hydrogen sulphide, sulphur dioxide or carbon monoxide.

2. In the method claimed in claim 1, the improvement wherein $0.3 \leq x \leq 0.1$.

3. In the method as claimed in claim 1, the improvement wherein said sensor element has a microstructure in which the average crystallite diameter and average pore diameter are both smaller than 1 micrometer.

4. In the method as claimed in claim 1, the further improvement wherein said sensor element includes a heating element for heating said sensor element, and electrical connecting means connected to said sensor element and said heating element, said connecting means comprising first connection means connected to said sensor element, and a common connecting means connected to both said sensor element and said heating element.

5. In the method as claimed in claim 4, the improvement wherein one of said elements is overlaid on the other of said elements so that said elements work as two resistors in parallel, said first connection means comprising a further connection common to both said elements.

6. In the method as claimed in claim 1, the improvement wherein said sensor comprises a sensor array, and said sensor element formed of $Cr_{(2-x)}Ti_xO_3$, constitutes a first sensor in said sensor array, and at least one further sensor element having a characteristic response different from the response of said first sensor.

7. In the method as claimed in claim 6, the further improvement wherein said further sensor element is formed of $Fe_{(1-y)}Cr_yNbO_4$, where $0 \leq y \leq 1$ for distinguishing between ammonia and organic vapor.

8. In the method as claimed in claim 6, the further improvement wherein said further sensor element is formed of $CrNbO_4$.

9. In the method as claimed in claim 6, the improvement wherein said further sensor element is formed of $SnO_2$.

10. In the method as claimed in claim 6, the further improvement wherein said further sensor has a sensor element formed of $BaSn_{(1-z)}Sb_2O_3$ where $0 \leq z \leq 0.1$, and said first sensor element is a sensor responsive to reactive an/or flammable gases but substantially non-responsive to carbon dioxide at low concentrations to which said further sensor shows a significant response.

11. In the method as claimed in claim 6, the improvement wherein said array includes a humidity sensor arranged for mitigating the effects of relative humidity.

* * * * *